United States Patent [19]
Elger et al.

[11] Patent Number: 5,614,213
[45] Date of Patent: Mar. 25, 1997

[54] USE OF ESTRIOL FOR TREATMENT OF CLIMACTERIC OSTEOPOROSIS

[75] Inventors: Walter Elger, Berlin; Birgitt Schneider; Michael Oettel, both of Jena; Michael Ernst, Jena/Lobeda Ost; Doris Hübler, Schmieden; Michael Dittgen, Apolda, all of Germany

[73] Assignee: EnTec Gesellschaft fuer Endokrinologische Technologie m.b.H., Germany

[21] Appl. No.: 295,723

[22] PCT Filed: Mar. 18, 1993

[86] PCT No.: PCT/EP93/00636

§ 371 Date: Aug. 31, 1994

§ 102(e) Date: Aug. 31, 1994

[87] PCT Pub. No.: WO93/18774

PCT Pub. Date: Sep. 30, 1993

[30] Foreign Application Priority Data

Mar. 21, 1992 [DE] Germany .......................... 42 09 295.7

[51] Int. Cl.⁶ ..................................................... A61F 13/00
[52] U.S. Cl. ............................................. 424/449; 514/969
[58] Field of Search ............................. 424/449; 514/969

[56] References Cited

U.S. PATENT DOCUMENTS

| | | | |
|---|---|---|---|
| 4,738,957 | 4/1988 | Laurent | 514/182 |
| 5,108,995 | 4/1992 | Casper | 514/170 |
| 5,116,828 | 5/1992 | Miura | 514/171 |

FOREIGN PATENT DOCUMENTS

| | | |
|---|---|---|
| 2001618 | 10/1989 | Canada . |
| 0370220 | 5/1990 | European Pat. Off. . |
| 3910578 | 10/1990 | Germany . |

OTHER PUBLICATIONS

Rudel et al; Oral Contraceptives: Human fertility studies and side effects, in Int. Encycl. Pharmacol of the Endocrine System CH, 34, London, Pergamon Press, 1972.
Lemon; Antimammary Cancerogenic Activity of 17α–ethinyl–estriol, Cancer, 60 2873–2881, 1987.
Follingstad; J. of the American Medical Assoc., 239, 29/30, 1978.
Blum et al; Clin. Exp. Obstet. Gynecol., 12 —1/2 1985.
Lindsay et al; Bone loss during oestriol therapy in postmenopausal women, in Maturitas 1, 279–285, 1979.
Brinton; "Menopause and . . . " N.Y. Acad. of Science, 592, pp 357–362, 1990.
Loboi; "Estrogen and Cardiovascular Disease" in Multidisciplinary Perspectives on Menopause, Annals of N.Y. Acad. of Science, 592 pp. 286–294, 1990.
Henderson, et al.; Richard and Hinda Rosenthal Fndtn Award Lecture, Cancer Research, 48, 246–253, 1988.
Clarke et al; "The role of steroid hormones . . . ", Nucl. Hormone Receptors, London Acad. Press, pp. 297–319–1991.
JP910116731 Abstract (1991).
Drugs vol. 39, No. 2, 1990 pp. 205–217 Sitruk–Ware "Estrogen Therapy During Menopause . . . Recommendations".
Maturitas, 12 (1990) 199–214 Lauritzen "clinical Use of oestrogens and progestogens".

Primary Examiner—D. Gabrielle Phelan
Attorney, Agent, or Firm—Nixon & Vanderhye

[57] ABSTRACT

The invention relates to the use of estriol as the sole active ingredient for the production of a transdermal medicament which continuously releases the active ingredient for the treatment of climacteric osteoporosis. It has been shown according to the invention that estriol, which has up until now been thought ineffective for the treatment of climacteric osteoporosis, develops strong anti-osteoporotic effectiveness upon continuous transdermal application.

4 Claims, 6 Drawing Sheets

Fig. 6

FREE ESTRIOL IN THE SERUM

DOSE: 12mg ESTRIOL CONTINUOUSLY OVER 24 HOURS

AVERAGE VALUES FROM 4 SUBJECTS

—○— TTS TYPE 34

—■— ESTRIOL EMULSION OINTMENT

USE OF ESTRIOL FOR TREATMENT OF CLIMACTERIC OSTEOPOROSIS

The invention relates to the use of estriol as sole active ingredient for the production of a transdermal medicament, which continuously releases the active ingredient, for the treatment of climacteric osteoporosis.

BACKGROUND OF THE INVENTION

The loss of the female sex hormone—estrogen—in the climacteric can lead to phenomena which require therapy. Estrogens are steroid hormones which are derived from the tetracyclic $C_{18}$ steroid estrane. Among the natural estrogens, one differentiates between estrone ($E_1$), estradiol ($E_2$) and estriol ($E_3$), estrone and estriol being the physiologically most important. Hormone replacement with both these estrogens quickly leads to an improvement in psychological consciousness and in the long term to a favourable influence on the bone and lipid metabolism. The last-mentioned factors represent effective prevention of diseases of the skeletal system and of illnesses of the heart circulation system. It has been proved without any doubt that $E_1$ and $E_2$ can prevent advancing osteoporosis in the climacteric and can slow the advance of arteriosclerotic vascular changes.

Against the said favourable effects there stands a risk, which is considered tolerable, from possible stimulating effects of the estrogens on the growth of hormone-dependent tumours of the genital tract (endometrium) and of the mammary gland. The known combination of estrogens with gestagens has the aim of minimizing the corresponding risks through the anti-proliferative action of gestagens in the uterus.

Examples of therapies with natural estrogens are:

1) The transdermal application of estradiol (for example Estraderm® TTS), 2) the oral application of estradiol and its esters, 3) the oral application of conjugated estrogens; these are obtained from the urine of gravid mares and are a mixture of different estrogens and 4) the vaginal application of natural estrogens. The latter aims to remedy atrophy of the genital mucous membranes.

As explained above, a disadvantage of therapy with such types of estrogens is their ability to cause uterine cancer (endometrium carcinoma) or breast cancer.

It has been proved that, by combining the aforementioned estrogens with a gestagen, the risk to those concerned of suffering an endometrium carcinoma is reduced to ⅙th of the risk to women treated only with estrogen. Examples of such combination therapies are described in DE-A-39 10 578, DE-A-39 08 130, DE 38 36 826 and EP 0 474 374.

However, a favourable effect on mortality from mastocarcinomas is not to be expected from a corresponding estrogen-gestagen combination. (L. A. Brinton "Menopause and . . . " New York, Academy of Sciences, 592, 357–362, (1990); R. A. Lobo, "Estrogen and Cardiovascular Disease" in "Multidisciplinary Perspectives on Menopause", published by M. Flint, F. Kronenberg and W. Utian, Annals of the N.Y. Acad. of Sciences, 592, pages 286–294 (1990)).

Breast cancer is the most frequent symptom of cancer in women over all. The theory is generally accepted that the mitogenic effect of the sum of the quantities of estrogen acting upon the mammary gland during life is a decisive (risk) factor for the occurrence of a cancerous disease of this organ (cf. B. E. Henderson, R. Ross and L. Bernstein "Estrogens as a cause of human cancer", The Richard and Hinda Rosenthal Foundation Award Lecture, Cancer Res., 48, 246–253, (1988); R. Clarke, R. B. Dickson and M. E. Lippman "The role of steroid hormones and growth factors in the control of normal and malignant breast" in "Nuclear Hormone Receptors", published by M. G. Parker, Academic Press, London, pages 297–319 (1991)).

The danger of the risk increase as regards illness from breast cancer is therefore a central factor in the assessment of the benefits and risks of hormone replacement therapy (HRT-Hormon Replacement Therapy; L. A. Brinton "Menopause and the risk of breast cancer", in Multidisciplinary Perspectives on Menopause. Ann, N.Y. Academy of Sciences, published by M. Flint, F. Kronenberg and W. Utian, 592, pages 357–362 (1990) review). In the case of longer-lasting therapy, various epidemiological studies suggested an increase in the relative risk by a factor of 1.5 to 3.1, the latter being in the cases where HRT had lasted more than 10 years (Table 3, page 359 of the aforementioned paper).

The situation is different in the case of estriol. On the one hand it is known that it can prevent or suppress the development of mastocarcinomas, but on the other hand it has hitherto been reported to have an inadequate therapeutic effectiveness within the scope of hormone replacement therapy (HRT). The latter has a particular importance for the prevention of osteoporosis. Thus, in an official statement by the Deutsche Gesellschaft für Endokrinologie, the ineffectiveness of estriol for osteoporosis prophylaxis is expressly emphasized (cf. Deutsches Ärtzeblatt—Ärztliche Mitteilungen, 85, 1322–1325, partic. 1325, 1-hand col.

Estriol is normally formed in the cycle and in pregnancy, whereby extraordinarily large quantities are expelled during pregnancy. From a pharmacological viewpoint, estriol is regarded as weakly-acting estrogen. The differences compared with $E_1$ and $E_2$ and with other synthetic estrogens are for example displayed by the fact that estriol does not significantly stimulate uterine weights when administered once to ovariectomized rats. Corresponding findings, which indicate little or no effect on the uterus, have also been made in studies involving women. Even comparatively high dosages of 5 mg $E_3$/day oral (H. W. Rudel and R. A. Kincl "Oral contraceptives. Human fertility studies and side effects" in "International Encyclopedia of Pharmacology and Therapeutics", Chapter 34, "Pharmacology of the Endocrine System and related drugs . . . ", edited by M. Tausk, Volume II, pages 385 et seq., Pergamon Press, London, (1972)) were not able to suppress ovulation in women, whilst this was clearly possible with estradiol and conjugated estrogens even at lower dosages.

However, in other test arrangements, in which estriol was applied in combination with "strong" estrogens, this substance proved to have an anti-estrogen action. Accordingly, estriol is itself estrogenous, but has an anti-estrogen action via the displacement of stronger estrogens from the receptor.

In particular, the proven anti-tumour effect of estriol in the induction and promotion phases of tumour development (H. M. Lemon, "Antimammary Cancerogenic Activity of 17α-ethinyl-estriol" Cancer 60, 2873–2881 (1987)) leads one to expect that no additional growth impetus at the tumour centre results from treatments which contain estriol in pharmacodynamically relevant formulation, but that, on the contrary, suitable therapy leads to a reduction in the mammatumour risk.

The properties of estriol, which are possibly not only unproblematical but even anti-carcinogenic compared with other estrogens, were discussed inter alia also by Foilingstad in "The Journal of the American Medical Association" 239, 29/30 (1978) and the clinical testing of this estrogen was recommended. Relevant comprehensive studies were carried out with 80 women in the postmenopausal stage over a period of 2 years by Lindsay et al. (R. Lindsay, D. M. Hart, A. MacLean, J. Garwood, A. C. Clark and A. Kraszewski (1979), Bone loss during oestriol therapy in postmenopausal women, Maturitas 1: 179), and the results were continuously evaluated throughout the test period, in particular as regards a possible anti-osteoporotic effectiveness of the substance with reference to bone mineral content. To the disappointment of the authors, it was shown that estriol developed no osteoprotective effectiveness in the bones of the treated women, even in dosage quantities of 12 mg/day oral. The ineffectiveness of estriol in the bones has now become standard knowledge in the relevant text books (cf. for example Freimut A. Leidenberger, "Klinische Endokrinologie für Frauenärzte", Springer Verlag 1992, where, on page 356, it states word for word:

Not effective for osteoporosis prophylaxis:

Estriol, the medicament can however clear psychovegetative symptoms and local findings in the genital area.

Reference is also made to the ineffectiveness of estriol for the indication discussed here in product information for preparations which contain estriol as active ingredient (cf. for example Jenapharm Arzneimittel: Sortima und Preise dated 01.07.1991, page 67).

Nor was this overall assessment influenced by the report produced by Blumin 1985 (cf. M. Blum, Clin. Exp. Obstet. Gynecol. 12, ½ (1985)) which describes a study involving 25 women in the postmenopausal phase. A vaginal cream containing 0.5 mg estriol/g was administered to the women before they went to sleep, daily for 2 weeks and then twice weekly in a quantity of 0.5 g in each case over a period of 4 months. An improvement was observed in some of the postmenopausal disorders, in particular the disorders connected with genitourinary atrophy and dyspareunia, whilst insomnia, sweating and hot flushes were not improved. Accordingly, it was necessary to additionally administer chlonidine to combat these symptoms. The author also investigated the ratio of calcium to creatinine and, from a slight reduction in this ratio during the investigative period, inferred an anti-osteoporotic action of the estriol. However, for a statement of this type, the investigative period was much too short, cf. Lindsay et al. op cit. and, moreover, this ratio alone is not meaningful since it depends inter alia on nutrition; investigations at the bone were not carried out or reported by Blum.

The fact that all cardia symptoms of the postmenopausal disorders in the study of estriol reported by Blum remained unaffected, with the result that chlonidine had to be additionally administered, suggests that the patients, as previously, suffered from estrogen deficiency.

On assessing the overall state of the art, it can therefore be established that estriol has hitherto been considered unsuitable by specialists for the treatment of climacteric osteoporosis.

It is the problem underlying the invention to provide means, with the help of which climacteric osteoporosis can be effectively combatted, without at the same time having to accept an increase in the risk of illness from breast cancer.

To solve the problem, it is proposed according to the invention to use estriol for the production of transdermal retard preparations which guarantee a continuous active ingredient release over at least 24 hours.

Surprisingly, it has been shown according to the invention that estriol is a strong and anti-osteoporotically effective estrogen if it is administered transdermally in a system which continuously releases the active ingredient for at least 24 hours. The basis of the invention is the surprising finding that, if $E_3$ is administered continuously, an unexpected phenomenon occurs as regards the blood level for the active ingredient. Estrogens and thus also estriol are inactivated in the liver through conjugation with glucuronic acid or sulphate. All findings to date indicate that estriol is inactivated extremely quickly (cf. H. Kuhl, "Pharmacokinetics of oestrogens and progesterons", MATURITAS 12, 171–197, esp. FIG. 4, p.178 (1990)). It has however been shown according to the invention that substantially constant level of the active form of the substance is established if the active ingredient is administered continuously. This is obviously independent of the total quantity of free and conjugated active ingredient (see below) and appears to conform to an endogenous regulatory mechanism activated through continuous administration. Thus, in the case of transdermal administration in the human random test (cf. Example 6) the surprising observation was made that after an initial increase, the concentration of the non-metabolized hormone in the blood remained almost constant over 24 hours, whilst the sum of the free active ingredient and the inactivated metabolite fluctuates greatly (cf. FIGS. 1 and 2). The measured blood concentrations of the free estriol fluctuate in a range which corresponds to the physiological concentrations of estrogen hormones in the cycle of the woman (approximately 50 to 350 pg/ml) and which are therefore suited to removing estrogen deficiency states in optimum manner.

The fact that the concentration of free estriol remains the same while the total estrogen level is changeable suggests that, with continuous introduction, some of the metabolized estriol is converted back into the starting product again, whereby, however, the conversion appears to be controlled in such a way that a constant level is ultimately reached. Further proof of the fact that the effect observed according to the invention is not linearly dependent on concentration, but based on an active regulatory mechanism, is the greatly fluctuating quotient of unconjugated and total estriol (cf. FIGS. 3 and 4). For the use according to the invention, this also offers an advantageous protective mechanism of the body against overdosing at the same time.

Figure 5:
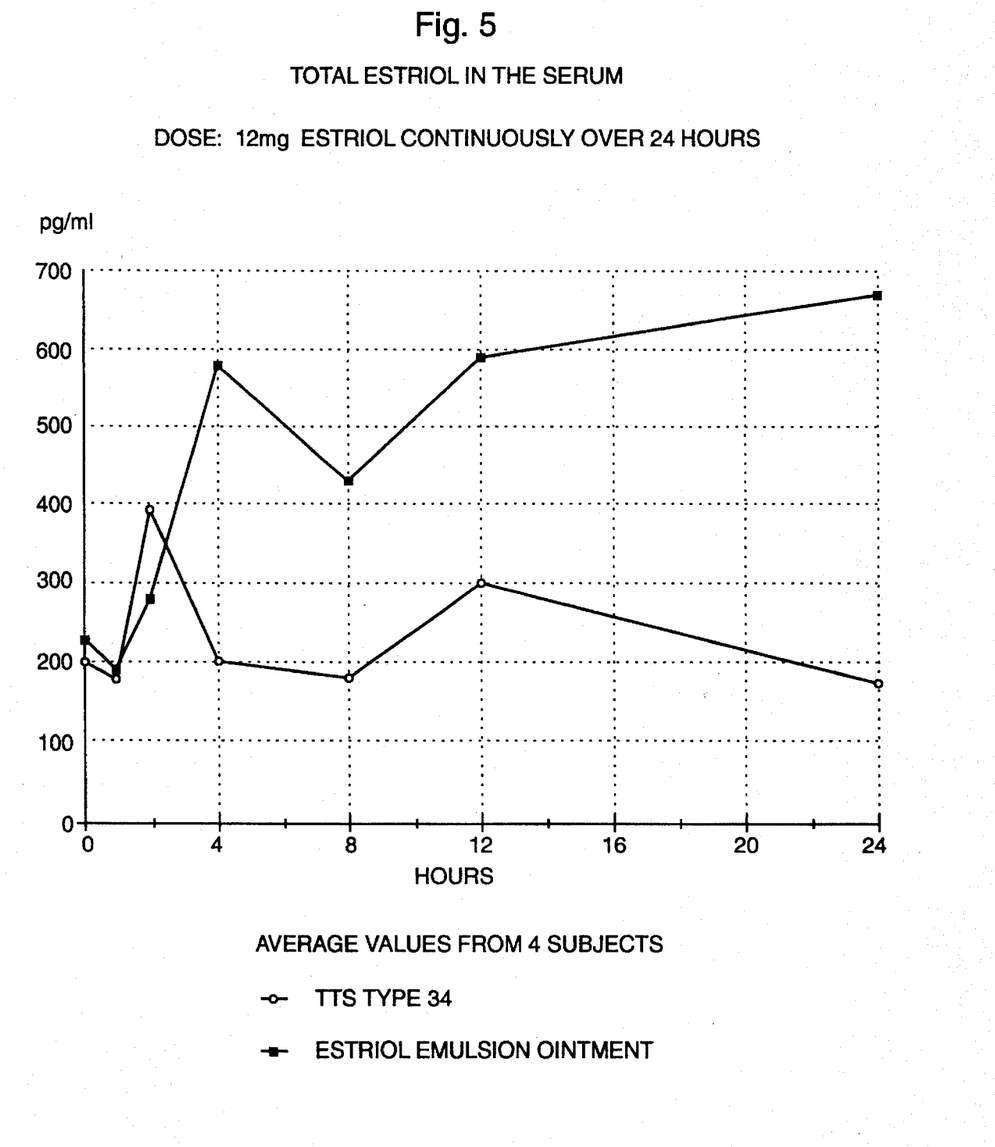
FIG. 5 is a graph comparing the total estriol in the blood serum over a period of 24 hours of an estriol emulsion ointment as compared with a transdermal formulation.

The finding according to the invention and the advantages of the teaching according to the invention deriving from this are confirmed by the results with various transdermal systems (see below). Whilst the total quantities of free and metabolized active ingredient fluctuated by a factor of 2 to 3, depending on the system, a practically identical pattern of the free estriol levels decisive for effectiveness was observed at the same time in a completely unexpected way (cf. FIGS. 5 and 6).

In contrast to the opinion held to date in the state of the art that estriol is a weak estrogen, it has been shown under the application conditions according to the invention that estriol is a decidedly strong estrogen. The findings according to the invention speak for estriol as the estrogen of choice for continuous hormone replacement therapy and in particular for the treatment of climacteric osteoporosis. In the case of continuous administration, osteoporosis is effectively treated or prevented on the one hand, whilst on the other hand the carcinogenic effect observed with traditional estrogens is missing, and even an anti-carcinogenic action can be expected.

According to the invention, all transdermal therapeutic systems—TTS—are suitable in principle which ensure continuous active ingredient release over at least 24 hours. Particularly preferred according to the invention are transdermal active ingredient plasters or transdermal emulsion ointments. Preferred dosing forms are those which in 24 hours release 5 to 25, preferably 10 to 15 and in a particularly preferred way 12 mg estriol per dosing unit.

A TTS according to the invention in the form of an active ingredient plaster is preferably designed as a simple matrix system. This means that the active ingredients are contained in a structure (reservoir), in which penetration-reinforcing agents can optionally also be contained. The matrix is located on a carrier film, preferably an aluminium film, and it is sealed off to the outside with a removable protective layer or a non-permeable cover sheet. If a cover sheet is used, this can, if desired, contain penetration-reinforcing agents.

A simple matrix system within the meaning of the invention can for example be prepared as follows:

A solution or suspension of 1 to 60 wt. % active ingredient is processed by adding from 0 to 45 wt. % of a penetration-reinforcing agent and 30 to 70 wt. % of a polyacrylate adhesive to the plaster. The polyacrylate adhesive can be dissolved in a suitable volatile solvent or dispersed in water. The mixture comprising active ingredient, penetration promoter and adhesive is coated onto a plane non-permeable aluminium film, dried and then provided with a removable protective layer, for example of siliconized fabric or fluoropolymer-coated paper.

If a polyacrylate is used which, after the system has dried, adheres insufficiently or not at all to the skin, the system can additionally be covered or enclosed with a contact adhesive, prior to applying the removable protective layer. A polyacrylate is likewise usually used as material for this contact adhesive. This procedure has the advantage that the layers can be brought into close contact during production or following subsequent joining under pressure (calendering). In this way, a layer system (laminate) is produced in which and from which the active ingredient can diffuse in favourable manner.

In an analogous way silicones, polyurethanes and natural or synthetic caoutchoucs can however also be used as materials for the matrix layer and the contact adhesive. As further additives to the matrix are celluloses and/or cellulose derivatives, polyvinyl compounds, silicones or silicates can be considered.

W/o emulsion systems (water/oil emulsion systems) are preferably used according to the invention as transdermally active ointments—TAO—. This means that the active ingredients can be added in the form of an aqueous solution, which can optionally contain a penetration promoter, to a w/o base conventionally used in pharmacy. The complete ointment exists in volumes which each correspond to a single dosage, in cavities which are formed from a suitable film, preferably a plastic film. The cavities are sealed with a removable protective layer. The prepared pack is in principle similar to a "blister pack".

The wool wax alcohol ointment of DAB 10 can for example be used as a simple w/o base within the meaning of the invention. If a suitable emulsifier is used, more complicated emulsions can also arise. Coming into consideration are also o/w/o or w/o/w/o systems, provided that they satisfy the prerequisites according to the invention, namely a continuous active ingredient release over at least 24 hours. It can sometimes happen that the emulsion adheres insufficiently to the skin or not at all, or penetrates into it. In this case, suitable adhesion-promoting additives or penetration-promoting agents can additionally be added to the outer phase. Used for example as penetration-promoting agent is a mono- or polyhydric alcohol. In the production of the ointment, one can start with an active ingredient solution or suspension which contains 1 to 60 wt. % estriol and this can be thickened with up to approximately 12 wt. % stabilizer. Aluminium stearate, bentonite, silicic acid or a silicon dioxide can for example serve as stabilizers.

The invention is explained below with reference to examples.

EXAMPLE 1

Formulation of a transdermally-active (TTS type 22) plaster

The plaster was produced from two formulations of the composition given below:

| Constituents | mg/plaster |
| --- | --- |
| Formulation I | |
| Estriol | 12 |
| Ethanol | 70 |
| Water | 18 |
| Formulation II | |
| Eudragit ® L 100 | 14 |
| Eudragit ® S 100 | 14 |
| Dye | 2 |
| Glycerine | 5 |
| Water | 65 |

Formulation I and formulation II are mixed. The mixture is spread thinly in a suitable way e.g. by casting process or by knife application, and dried to give the film. A suitable adhesive layer (e.g. made from Durotac®) is deposited on the dried film in a thin layer, so that a laminate results. The laminate is then dried again.

It is also possible to produce the laminate in the so-called "transfer process" by calendering the film which contains the drugs with a suitable adhesive film. Prior to using the transdermal plaster, the adhesive layer can be covered in a known way with a protective film.

The transdermal plaster adheres to human skin, even if it slightly hairy. The active ingredients contained can diffuse through the adhesive film, penetrate into the skin and become systemically active.

EXAMPLE 2

Formulation of a transdermally active plaster (TTS-type 34)

The procedure according to Example 1 was repeated, with the difference that instead of Eudragit® L100 and S100 a total of 28 mg Softisan® TSD 34M15/3A were used.

EXAMPLE 3

Production of a transdermally active emulsion ointment

An impermeable film was shaped by heat and/or tension such that a 0.1 to 3 ml capacity blister was formed. This was filled with the ointment. The ointment contained an active ingredient-containing solution or suspension in a concentration of 12 mg estriol per 0.5 g ointment. The latter was prepared from two different formulations as given below:

| Constituents | mg/0.5 g ointment |
| --- | --- |
| Formulation I | |
| Estriol | 12 |
| Ethanol | 7 |
| Water | 81 |
| Formulation II | |
| Water | 30 |
| Glycerine | 15 |
| medium-chained triglycerides | 55 |
| Wool wax alcohol ointment | 400 |

Formulation II was homogenized and heated in a water bath to 60° C. Formulation I, which had been heated to the same temperature, was then incorporated in portions into the homogenized mixture.

In each case, 0.5 g of ointment are poured into a cavity of a film (blister), formed as described above, and sealed.

EXAMPLE 4

Investigation of the osteoporotic action of estriol on ovariectomized rats

1. Formulation of the question 11 week-old female Wistar rats lose a considerable proportion of their bone substance in two weeks after ovariectomy. It was to be investigated whether this effect is preventable through estriol. For this, this hormone was to be applied such that constant hormone levels are established over the whole test period. The procedure was based on the hypothesis that the hitherto-observed absence of an effect at the bone under estriol treatment was possibly due to a decrease below a critical hormone level in the blood between two application time points in the case of treatment forms as e.g. daily oral application. The assumption that estriol has insufficient activity as a partial estrogen antagonist at the bone was also to be examined as another possibility.

2. Material and methods

Female Wistar rats from the experimental animal breeders "Biomodelle GmbH", O-1291 Schönwalde (breed: Wistar) were supplied at ages from nine to ten weeks and kept under conventional conditions at a room temperature of 22° C.±24° C. and under a light regime (14 h light and 10 h dark) in PVC shells with fitted wire covers.

The animals received standard formulation R 13 feed and drinking water ad libitum.

At the age of 11 weeks (body weight approximately 220 g) the animals were used in the experiment.

3. Application of the test substance

Subcutaneous application osmotic pumps. Model: Alzet 2002, capacity of the reservoir 200 μl. Throughflow 0.5 μl/hour. Solution of the test substance in propylene glycol.

The duration of the whole experiment was 3 weeks, 1 week before castration and two weeks (15 days) after castration.

In the week prior to castration, characteristic parameters were determined "as starting values" prior to the estrogen-specific bone degradation through ovariectomy (hydroxyproline content in the 24-h-urine, hydroxyproline content and estriol concentration in the serum).

For the determination of the hydroxyproline content in the urine, the collective urine was obtained over 24 hours. For this, the animals were individually placed once a week in diuresis cages which permitted a sufficiently clean collection of urine, separate from faeces. The hydroxyproline content was then determined in the collective urine of each individual animal.

Hydroxyproline and estriol levels were determined in the serum which was obtained from the retrobulbar venous plexus on the same day as, and on the seventh and fourteenth days after, castration.

4. Investigation of the effects of estriol at the bones

At the end of the experiment the animals were killed and the femur bones fixed for histological investigations according to standard methods, cut with a hard cut microtome and investigated qualitatively and quantitatively as regards morphological features.

5. Test results

The test results are shown in Tables 1 to 4.

6. Evaluation

The outcome of the experiments shows that this substance has an osteoprotective potential—in contrast to that stated for estriol in the literature.

According to the present experiments, a prerequisite for this effect is the creation of uniform levels of active ingredient. The results obtained led to the estriol therapy proposed according to the invention.

TABLE 1

| Test group name | N | Test groups Conditioning | Treatment | Dose/ 24 hrs |
| --- | --- | --- | --- | --- |
| SHO + V (intact controls) | 8 | OP light | Propylene glycol | |
| OVX + V (control) | 8 | castr. | " | |
| OVX + D1 | 8 | castr. | estriol | 0.1 μg |
| OVX + D2 | 8 | castr. | in | 1.0 μg |
| OVX + D3 | 8 | castr. | propylene glycol | 10.0 μg |
| OVX + D4 | 9 | castr. | | 50.0 μg |

Results

1. Hydroxyproline excretion in urine, hydroxyproline level in serum

Hydroxyproline is released during the decomposition of collagen which also accounts for a considerable proportion of the bone substance.

After ovariectomy, increasing hydroxyproline values were determined in the blood (Table 2); this increase was suppressed through treatment with estriol in dose-dependent manner.

Likewise, the excretion of hydroxyproline in the urine increases after castration. This effect can also be alleviated through treatment with estriol (Table 3).

TABLE 2

Hydroxyproline content (μmol/l l] in the serum of light-operated (SHO) and castrated (OVX) Wistar rats after estriol application (by bolus implantation)

| Dose | | Days after castration | | |
|---|---|---|---|---|
| | | 0 | 7 | 15 |
| SHO + V | X | 30,59 | 28,05 | 25,04 |
| (n = 8) | s | 4,46 | 2,82 | 5,50 |
| relative change [%] | X | | −6,47 | −16,69 |
| OVX + V | X | 29,92 | 40,35 | 39,41 |
| (n = 8) | s | 4,32 | 3,71 | 3,72 |
| relative change [%] | X | | 36,71 | 33,77 |
| OVX + D1 | X | 30,55 | 35,31 | 33,36 |
| (n = 8) | s | 4,78 | 4,11 | 6,91 |
| relative change [%] | X | | 18,44 | 11,66 |
| OVX + D2 | X | 30,74 | 33,20 | 30,51 |
| (n = 8) | s | 3,03 | 3,63 | 5,10 |
| relative change [%] | X | | 8,82 | 0,39 |
| OVX + D3 | X | 28,16 | 26,25 | 20,90 |
| (n = 8) | s | 4,85 | 3,52 | 1,58 |
| relative change [%] | X | | −3,56 | −23,81 |
| OVX + D4 | X | 28,26 | 25,45 | 17,33 |
| (n = 9) | s | 3,17 | 3,85 | 3,32 |
| relative change [%] | X | | −8,87 | −38,62 | n* = number of animals
X = average value
s = standard deviation

TABLE 3

Hydroxyproline content (μmol/l d] in the urine of light-operated (SHO) and castrated (OVX) Wistar rats after estriol application (by bolus implantation)

| Dose | | Days after castration | | | | | |
|---|---|---|---|---|---|---|---|
| | | 0 | 7 | 12 | 13 | 14 | 15 |
| SHO + V | X | 1,62 | 1,67 | 1,91 | 1,40 | 1,75 | 1,10 |
| (n = 8) | s | 0,38 | 0,83 | 0,63 | 0,93 | 0,65 | 0,43 |
| relative change [%] | X | | 4,34 | 22,02 | −17,13 | 6,83 | −29,13 |
| OVX + V | X | 1,82 | 1,92 | 2,80 | 2,35 | 2,81 | 1,85 |
| (n = 8) | s | 0,42 | 0,48 | 0,85 | 1,02 | 1,03 | 1,51 |
| relative change [%] | X | | 7,58 | 57,30 (n = 7) | 26,73 | 59,37 | 4,69 |
| OVX + D1 | X | 1,46 | 2,15 | 2,41 | 2,51 | 2,11 | 2,00 |
| (n = 8) | s | 0,46 | 0,75 | 0,93 | 0,72 | 0,87 | 0,85 |
| relative change [%] | X | | 56,95 | 84,62 | 79,03 | 59,47 | 40,95 |
| OVX + D2 | X | 1,63 | 1,94 | 2,97 | 2,40 | 2,31 | 1,83 |
| (n = 8) | s | 0,36 | 0,57 | 1,36 | 1,05 | 1,23 | 0,85 |
| relative change [%] | X | | 15,48 | 74,86 | 42,71 | 37,83 | 10,69 |
| OVX + D3 | X | 1,67 | 0,88 | 0,98 | 1,04 | 0,94 | 1,16 |
| (n = 8) | s | 0,20 | 0,47 | 0,27 | 0,22 | 0,34 | 0,62 |
| relative change [%] | X | | 47,88 | −40,47 | −36,63 | −48,91 | −28,45 |
| OVX + D4 | X | 1,53 | 0,99 | 1,09 | 1,06 | 0,98 | 0,93 |
| (n = 8) | s | 0,40 (r = 9) | 0,36 (n = 9) | 0,57 | 0,37 | 0,21 | 0,30 |
| relative change [%] | X | | −34,52 | −33,26 | −35,04 | −38,21 | −40,43 |

TABLE 4

Effects of an estriol treatment on the trabecular proportion of the bone volume after ovariectomy

| Treatment | % trabecular proportion |
|---|---|
| OP light, vehicle treatment (= intact control) | 25.44 |
| Ovariectomy (OVX), Vehicle treatment | 14.40 |
| OVX + 0.1 microg $E_3$[1]/day | 16.89 |
| OVX + 1.0 microg $E_3$[1]/day | 17.46 |
| OVX + 10.0 microg $E_3$[1]/day | 24.79 |
| OVX + 50.0 microg $E_3$[1]/day | 26.64 |

[1] $E_3$ = estriol

2. Effects on the bone substance:

The effect on the proportion of trabecular structures in the surface of bone sections was determined as a parameter of the osteoprotective effect of estriol. It is evident from Table 4 that a considerable proportion of the bone mass is decomposed after castration. This effect was alleviated by estriol in a dose-dependent manner.

EXAMPLE 5

Pilot study of the blood level pattern of estriol after transdermal application on healthy male subjects It was the aim of the study to investigate the estriol serum concentration in the case of continuous administration from different transdermal systems over several hours. The type of study corresponded to a Phase I clinical test (pilot study) which had been examined by the Ethics Commission of the Friedrich Schiller University, Jena and had been approved for implementation.

The clinical test was carried out on healthy men, since the subject of the investigation was the pharmaceutical properties of the formulation and not the metabolism of the active substance in the organism. All factors which could disturb comparability as regards absorption, distribution, metabolism and elimination therefore had to be excluded. Because of this, individuals with an own and possibly fluctuating basal level of the hormone to be investigated, i.e. female subjects, were not suitable for this study.

Test preparations:

Three different transdermal formulations were tested, each of which contained 12 mg estriol:

1. TTS-TVDe 22:

Plaster with a diameter of 32 mm, covering layer of aluminium, estriol reservoir and adhesive layer made from polyacrylate (reservoir: Scopacryl®, Buna GmbH; adhesive layer: Durotac®, Delft National Corp.). The estriol was distributed in molecularly disperse manner in the reservoir and partially in the contact layer.

2. TTS-TVDe 34:

Plaster with a diameter of 56 mm, covering layer made from flesh-coloured tissue, estriol reservoir as disk with a diameter of 36 mmin the centre, estriol reservoir consists of a sponge-like material (Softisan® TSD 34M15/3A), in which estriol is present in finely dispersed form, adhesive layer made from usual plaster adhesive.

3. Estriol-TAO:

Cream with an active ingredient concentration of 12 mg estriol/0.5 g.

Type and scope of the study:

Three groups were formed, each of 4 healthy men aged between 18 and 55 years. Each group was allocated one of the test preparations, whereby the plaster was stuck on in the region of the gluteal muscle and the gel massaged in in the forehead region. The test preparations were administered at chronologically parallel times and the groups allocated according to a randomisation list. The random numbers were assigned sequentially according to the order of inclusion of the subjects into the study. Blood samples were taken at the time points 0, 0.5, 1, 2, 4, 8, 12 and 24.

Course of the investigation:

The test preparations were administered on the day of the test at 8 o'clock in the morning. To evaluate the estriol plasma level, 10 ml of blood were removed in each case at the given times, the serum was separated by means of centrifugation and stored at −20° C. until the hormone concentration was determined.

Hormone determination:

The total estriol and free estriol were determined by means of RIA technology (Amersham-RIA) in the hormone laboratory of Tübingen Universitätsfrauenklinik. For the determination of the total estriol level, the sera were incubated initially with glucoronidase/sulphatase-solution and the released diconjugated estriol extracted with ether. The RIA determination was then carried out with the extracts absorbed in the buffer. Free estriol was extracted direct from non-pretreated subjects and determined in the same way.

Evaluation:

The concentration of free and total estriol in the serum of the subjects was determined. The total estriol includes free and metabolized estriol. For each subject, the following parameters were determined from the chronological pattern:

AUC: Area under the concentration time curve which is calculated with the trapezium rule (time point 0 to 24 hours)

Figure 1:
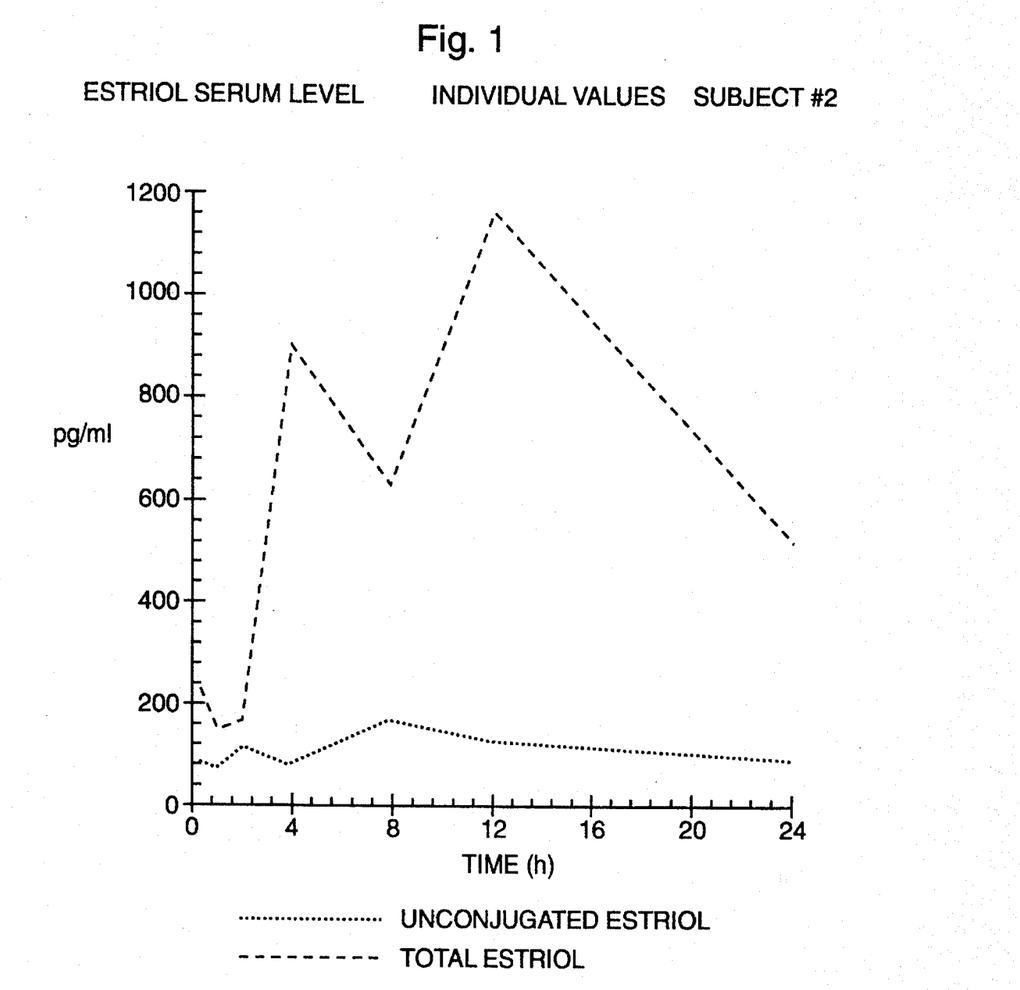
FIG. 1 is a graph for subject No. 2 of the estriol serum level for both unconjugated estriol and total estriol over a period of 24 Hours.
Figure 2:
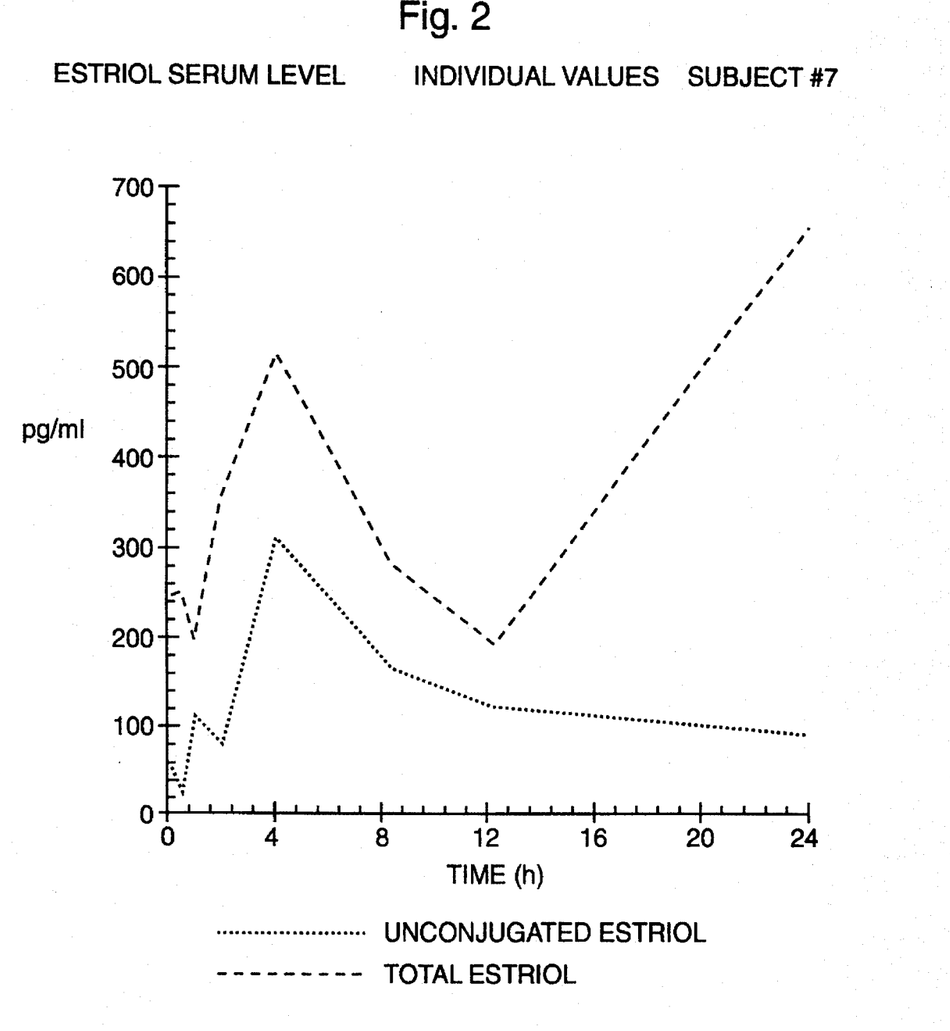
FIG. 2 is graph for subject No. 7 of the estriol serum level for both unconjugated estriol and total estriol over a period of 24 Hours.
Figure 3:
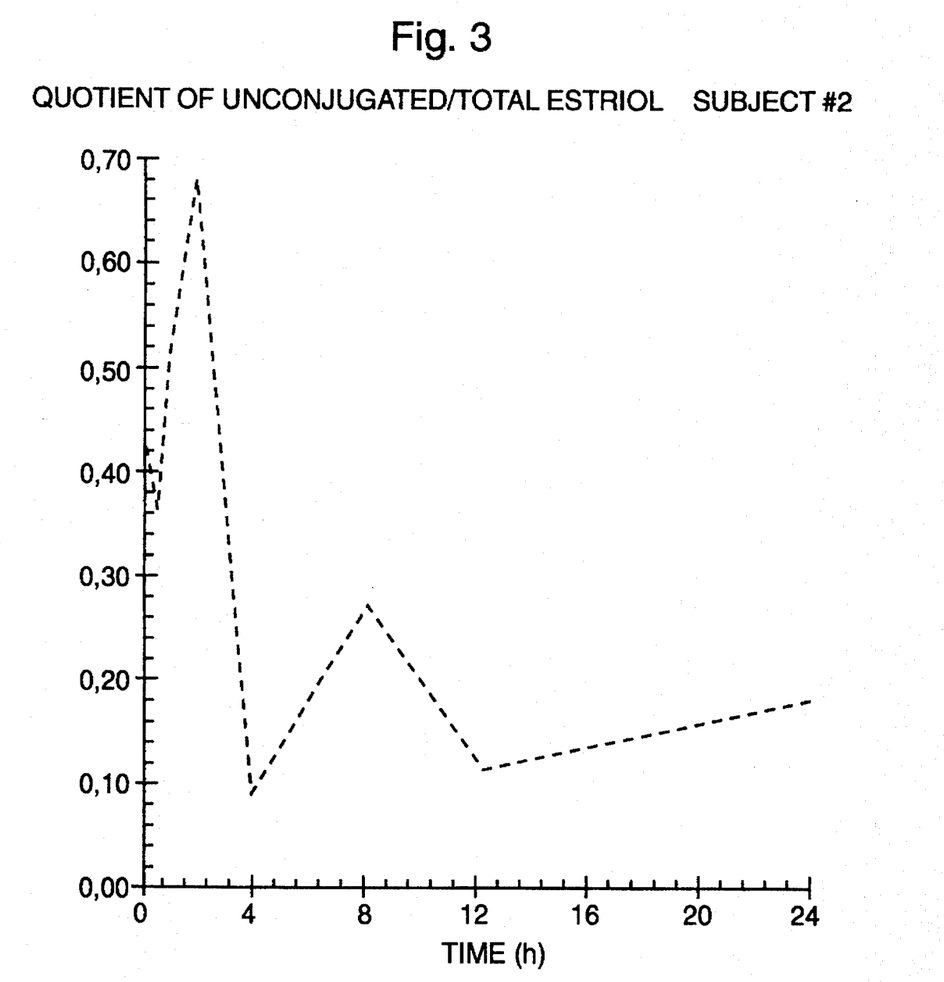
FIG. 3 is a graph showing the quotient of unconjugated estriol over total estriol for subject No. 2 over 24 hours.
Figure 4:
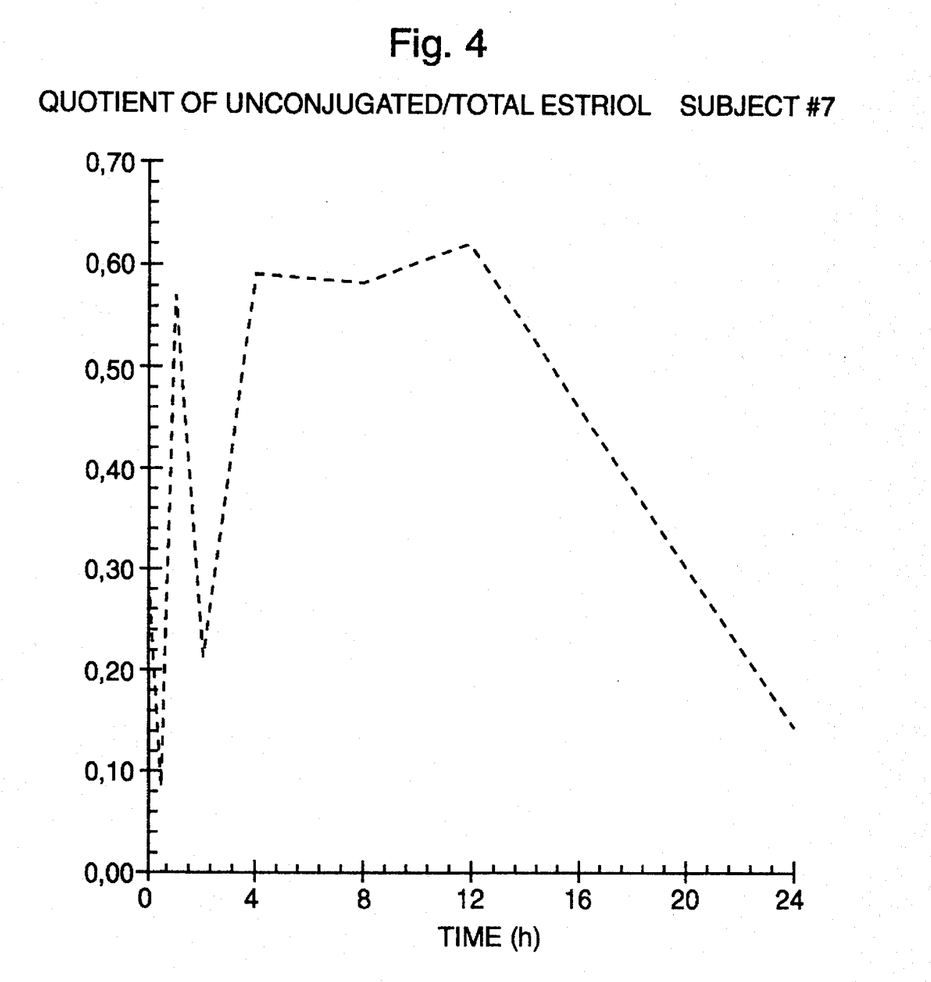
FIG. 4 is a graph showing the quotient of unconjugated estriol over total estriol for subject No. 7 over 24 hours.

$C_{max}$: Concentration maximum $T_{max}$: time until the maximum has been achieved Results:

The study led to the unexpected result that the curve of the total quantity of active ingredient and metabolized active ingredient in the blood (total estriol in the serum) after transdermal application of all three systems shows an irregular pattern between the different measuring time points (cf. FIGS. 1 and 2, corresponding to subjects 2 and 7). It is completely surprising under these conditions that, after the initial increase, the concentration of the therapeutically active, non-metabolized hormone (unconjugated estriol) remains almost constant over 24 hours (FIGS. 1 and 2 corresponding to subjects 2 and 7), whilst the quotient of free and total estriol fluctuates markedly (FIGS. 3 and 4 corresponding to subjects 2 and 7).

The measured blood concentrations of the free estriol move in an interesting way in the range which corresponds to the physiological concentrations of estrogen hormones in the cycle of the women (approximately 50 to 350 pg/ml). It is therefore to be assumed that all investigated transdermal systems are suitable for alleviating estrogen deficiency states in optimum manner.

Figure 6:
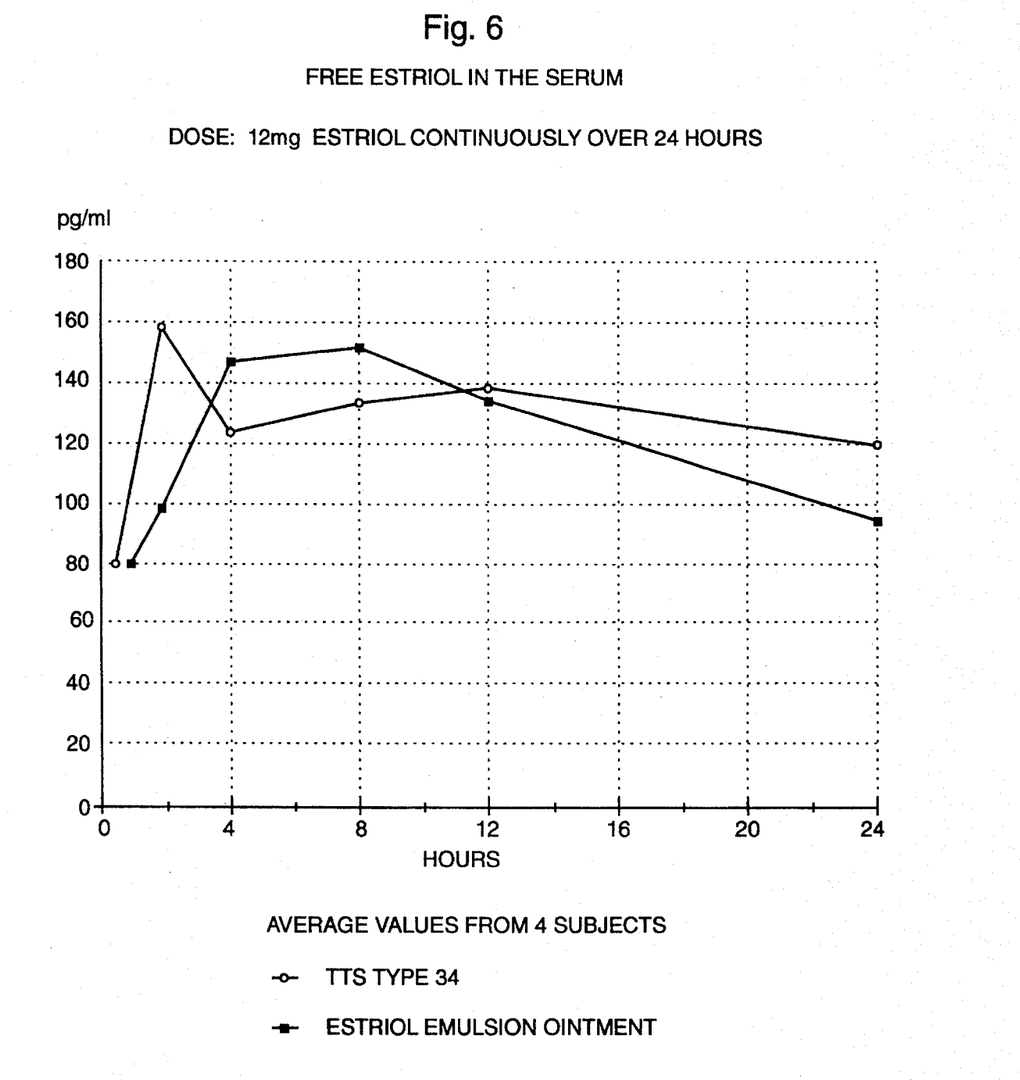
FIG. 6 is a graph comparing the free estriol over a 24 hour period in the serum of the same four patients (averaged) as in FIG. 5 using the same formulations.

This is all the more valid since the different formulations led to different total serum estriol concentrations (cf. FIG. 5), whereby the concentrations of the transdermal retard emulsion gel lay above the System TTS Type 34 by a factor of 2 to 3, but, surprisingly, a practically identical pattern of the estriol levels which are alone relevant (non-conjugated serum estriol) was observed, cf. FIG. 6.

The result of the pilot study described above leads one to assume that in the case of continuous administration of estriol, endogenous mechanisms have a "regulating" effect on the measured estriol level in the blood, which leads to obvious advantages in the choice of estriol for hormone replacement therapy and in particular for the treatment of climacteric osteoporosis, since for example an overdose appears to be largely excluded.

We claim:

1. A method of treating climacteric osteoporosis comprising continuously transdermally administering from 5 to 25 mg per day of estriol as the sole active ingredient to a person in need of same for at least 24 hours.

2. The method of claim 1 in which the estriol is administered from a transdermal patch.

3. The method of claim 1 in which the estriol is administered from a transdermal emulsion ointment.

4. The method of claim 2 or 3 in which the transdermal patch or ointment contains 5 to 25 mg of estriol per unit dose.

* * * * *